United States Patent
Im et al.

(10) Patent No.: US 10,870,104 B2
(45) Date of Patent: Dec. 22, 2020

(54) METHOD FOR PREPARING OLIGOMERIZATION CATALYST SYSTEM AND OLIGOMERIZATION CATALYST SYSTEM PREPARED THEREBY

(71) Applicant: LG CHEM, LTD., Seoul (KR)

(72) Inventors: Seul Ki Im, Daejeon (KR); Yong Ho Lee, Daejeon (KR); Eun Ji Shin, Daejeon (KR); Jin Young Park, Daejeon (KR); Seok Pil Sa, Daejeon (KR); Ki Soo Lee, Daejeon (KR)

(73) Assignee: LG CHEM, LTD., Seoul (KR)

(*) Notice: Subject to any disclaimer, the term of this patent is extended or adjusted under 35 U.S.C. 154(b) by 48 days.

(21) Appl. No.: 15/528,576

(22) PCT Filed: Feb. 2, 2016

(86) PCT No.: PCT/KR2016/001146
§ 371 (c)(1),
(2) Date: May 22, 2017

(87) PCT Pub. No.: WO2016/129847
PCT Pub. Date: Aug. 18, 2016

(65) Prior Publication Data
US 2018/0339289 A1 Nov. 29, 2018

(30) Foreign Application Priority Data

Feb. 12, 2015 (KR) .................. 10-2015-0021784
Aug. 24, 2015 (KR) .................. 10-2015-0118964

(51) Int. Cl.
| | | |
|---|---|---|
| C07C 2/32 | (2006.01) | |
| B01J 31/24 | (2006.01) | |
| C08K 5/00 | (2006.01) | |
| C08K 5/17 | (2006.01) | |
| B01J 31/18 | (2006.01) | |
| B01J 31/02 | (2006.01) | |
| B01J 31/04 | (2006.01) | |
| B01J 31/14 | (2006.01) | |
| C08F 210/16 | (2006.01) | |
| C07C 2/24 | (2006.01) | |
| C08F 2/40 | (2006.01) | |
| C08F 4/69 | (2006.01) | |
| C08F 10/00 | (2006.01) | |
| C08K 5/05 | (2006.01) | |
| C07F 9/50 | (2006.01) | |
| B01J 35/00 | (2006.01) | |
| B01J 37/04 | (2006.01) | |
| C08F 10/02 | (2006.01) | |

(52) U.S. Cl.
CPC ....... B01J 31/2409 (2013.01); B01J 31/0267 (2013.01); B01J 31/04 (2013.01); B01J 31/143 (2013.01); B01J 31/187 (2013.01); B01J 31/188 (2013.01); B01J 35/0006 (2013.01); B01J 37/04 (2013.01); C07C 2/24 (2013.01); C07C 2/32 (2013.01); C07F 9/505 (2013.01); C07F 9/5022 (2013.01); C08F 2/40 (2013.01); C08F 4/69 (2013.01); C08F 10/00 (2013.01); C08F 10/02 (2013.01); C08F 210/16 (2013.01); C08K 5/00 (2013.01); C08K 5/05 (2013.01); C08K 5/17 (2013.01); B01J 2231/12 (2013.01); B01J 2231/20 (2013.01); B01J 2523/67 (2013.01); B01J 2531/004 (2013.01); B01J 2531/31 (2013.01); B01J 2531/62 (2013.01); C07C 2523/26 (2013.01); C07C 2531/04 (2013.01); C07C 2531/14 (2013.01); C07C 2531/18 (2013.01); C07C 2531/22 (2013.01); C07C 2531/24 (2013.01)

(58) Field of Classification Search
CPC .................................. C07C 2/32; B01J 31/24
See application file for complete search history.

(56) References Cited

U.S. PATENT DOCUMENTS

| | | | |
|---|---|---|---|
| 5,420,373 A | 5/1995 | Hope et al. | |
| 5,550,307 A | 8/1996 | Hope et al. | |
| 5,817,899 A | 10/1998 | Hope et al. | |
| 2006/0247483 A1 | 11/2006 | McConville et al. | |
| 2008/0027188 A1 | 1/2008 | Small et al. | |

(Continued)

FOREIGN PATENT DOCUMENTS

| | | |
|---|---|---|
| CN | 101511851 A | 8/2009 |
| CN | 103270006 A | 8/2013 |

(Continued)

OTHER PUBLICATIONS

Kuhlmann, et al.: "Influence of Elevated Temperature and Pressure on the Chromium-Catalysed Tetramerisation of Ethylene", XP055438670, Advanced Synthesis & Catalysis, vol. 348, No. 10-11, Jul. 2006, pp. 1200-1206.

(Continued)

*Primary Examiner* — Caixia Lu
(74) *Attorney, Agent, or Firm* — Dentons US LLP

(57) ABSTRACT

The present invention relates to a method for preparing an oligomerization catalyst system and the method comprises preparing a catalyst composition by mixing a PNP-based ligand compound and a transition metal compound, and mixing and activating a co-catalyst and the catalyst composition at a temperature from −40 to 80° C. The oligomerization catalyst system prepared by the method may maintain the activity thereof during an oligomerization reaction at a high temperature, and the reaction temperature of oligomerization may be easily controlled. Various merits in processing may be obtained.

11 Claims, No Drawings

(56) References Cited

U.S. PATENT DOCUMENTS

| | | |
|---|---|---|
| 2008/0207857 A1 | 8/2008 | Small et al. |
| 2008/0293899 A1 | 11/2008 | McConville et al. |
| 2012/0172645 A1 | 7/2012 | Sydora |
| 2015/0011382 A1 | 1/2015 | Kwon et al. |
| 2015/0018502 A1 | 1/2015 | Kwon et al. |
| 2015/0298110 A1 | 10/2015 | Cho et al. |
| 2016/0122371 A1 | 5/2016 | Lee et al. |

FOREIGN PATENT DOCUMENTS

| | | |
|---|---|---|
| EP | 2987783 A1 | 2/2016 |
| JP | 7-310078 A | 11/1995 |
| KR | 10-2013-0126518 A | 11/2013 |
| KR | 10-2013-0142151 A | 12/2013 |
| KR | 10-2014-0063346 A | 5/2014 |
| WO | 2006/096881 A1 | 9/2006 |

OTHER PUBLICATIONS

Anthea Carter et al., "High activity ethylene trimerisation catalysts based on diphosphine ligands", Chemical Communications, 2002, vol. 8, pp. 858-859.

METHOD FOR PREPARING OLIGOMERIZATION CATALYST SYSTEM AND OLIGOMERIZATION CATALYST SYSTEM PREPARED THEREBY

CROSS-REFERENCE TO RELATED APPLICATIONS

This application is a National Stage Application of International Application No. PCT/KR2016/001146 filed on Feb. 2, 2016, which claims the benefit of Korean Patent Application No. 10-2015-0021784 filed on Feb. 12, 2015 and Korean Patent Application No. 10-2015-0118964 filed on Aug. 24, 2015, all of which are hereby incorporated by reference in their entirety for all purposes as if fully set forth herein.

TECHNICAL FIELD

Technical Field

The present invention relates to a method for preparing an oligomerization catalyst system of which activity may be maintained in an oligomerization reaction at a high temperature, and an oligomerization catalyst system prepared thereby.

Background Art

Linear alpha-olefin is an important material used in a comonomer, a cleaner, a lubricant, a plasticizer, etc. and is commercially and widely used. Particularly, 1-hexene and 1-octene are widely used as the comonomer for controlling the density of polyethylene during preparing linear low-density polyethylene (LLDPE).

In a preparation process of common LLDPE, copolymerization of alpha-olefins, for example, 1-hexene, 1-octene, etc. with ethylene is performed to control density by forming branches on a polymer backbone.

Accordingly, in the preparation of LLDPE having a high comonomer content, the comonomer is a costly part. To solve the drawback, various methods have been conducted.

In addition, the application field or the market size of alpha-olefins is dependent on the kind thereof, and technique on selective production of a specific olefin is commercially very important. Recently, researches on a technique using a chromium catalyst for preparing 1-hexene or 1-octene with high selectivity via selective ethylene oligomerization are being actively conducted.

Conventional and commercial preparation methods of 1-hexene or 1-octene include a shell higher olefin process (SHOP) of Shell Chemicals, a Ziegler process of Chevron Philips chemical, etc. Through the methods, alpha-olefins having a wide distribution of C4-C20 may be obtained.

As a catalyst for trimerizing ethylene, a chrome-based catalyst using a ligand having a formula of (R1) (R2)X—Y—X(R3) (R4) is suggested. In the formula, X is phosphor, arsenic or antimony, Y is a linking group such as —N(R5)-, and at least one of R1, R2, R3 and R4 have a polar or electron donating substituent.

In addition, a compound of (o-ethylphenyl)$_2$PN(Me)P(o-ethylphenyl)$_2$ including no polar substituent for at least one of R1, R2, R3 and R4 has been studied as a ligand not exhibiting catalyst activity to 1-hexene under catalytic conditions (*Chem. Commun.*, 2002, 858).

However, the conventional ligand including a heteroatom is still required to have consistent and continuous activity on multimerization reaction and high selectivity during preparing 1-octene or 1-hexene.

PRIOR ARTS

Non-Patent Document

1. *Chem. Commun.*, 2002, 858

DISCLOSURE OF THE INVENTION

Technical Problem

In the present disclosure, provided is a method for preparing an oligomerization catalyst system of which activity is not deteriorated but maintained at a high temperature during an oligomerization reaction by controlling the activation temperature and time of a catalyst composition including a ligand compound and a transition metal compound, and a co-catalyst, and an oligomerization catalyst system prepared thereby, and provided also is a method for oligomerization by which a temperature range controllable during an oligomerization reaction is wide, and diverse merits in process may be obtained.

Technical Solution

According to an aspect of the present invention, there is provided a method for preparing an oligomerization catalyst system comprising preparing a catalyst composition by mixing a ligand compound comprising a diphosphine moiety represented by Formula 1, and a transition metal compound, and mixing and activating a co-catalyst and the catalyst composition at a temperature from −40 to 80° C.

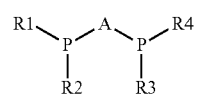

[Formula 1]

In Formula 1, A is N, As or Sb, R1 to R4 are each independently hydrocarbyl, heterohydrocarbyl or hydrocarbylheteryl having 1 to 20 carbon atoms.

In an embodiment, an activating time of the co-catalyst and the catalyst composition may be less than five minutes.

In an embodiment, an activating time of the co-catalyst and the catalyst composition may be three minutes or less.

In an embodiment, an activating temperature may be from 20 to 80° C.

In an embodiment, the activity of the catalyst system may be 100,000 kg/molCr/hr or more.

In an embodiment, an activity decreasing ratio of the catalyst system according to temperature increase may be less than 6% in a temperature range of an oligomerization reaction of 30 to 150° C.

In an embodiment, the ligand compound may comprise at least two diphosphine moieties represented by the following Formula 2, and a linker connecting the at least two diphosphine moieties may be hydrocarbyl having a carbon number of the shortest distance between the diphosphine moieties may be from 2 to 30.

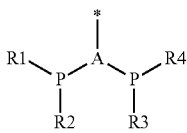

In Formula 2, A, and R1 to R4 are the same as in Formula 1, and * is a linker connecting at least two diphosphine moieties.

In an embodiment, the linker may be combined with at least one group selected from the group consisting of an aliphatic group having 1 to 20 carbon atoms, a heteroaliphatic group having 2 to 20 carbon atoms, an alicyclic group having 3 to 20 carbon atoms, a heteroalicyclic group having 3 to 20 carbon atoms, an aromatic group having 6 to 20 carbon atoms, and a heteroaromatic group having 6 to 20 carbon atoms, and the linker may comprise at least one group selected from the group consisting of an aliphatic group having 1 to 20 carbon atoms, a heteroaliphatic group having 2 to 20 carbon atoms, an alicyclic group having 3 to 20 carbon atoms, a heteroalicyclic group having 3 to 20 carbon atoms, an aromatic group having 6 to 20 carbon atoms, and a heteroaromatic group having 6 to 20 carbon atoms, as a substituent.

In an embodiment, the ligand compound may comprise a compound represented by the following Formula 3.

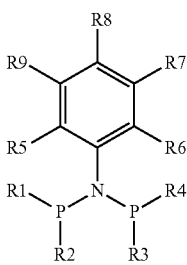

In Formula 3, R1 to R4 are the same as defined in Formula 1.

R5 is alkyl having 1 to 20 carbon atoms.

In the case that R5 is methyl, R6 is a linear group of alkyl, alkenyl, heteroalkyl, heteroalkenyl, or a heteryl group thereof having 2 or 3 carbon atoms; alkyl, alkenyl, arylalkyl, arylalkenyl, heteroalkyl, heteroalkenyl, heteroarylalkyl, heteroarylalkenyl, or a heteryl group thereof having 4 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

In the case that R5 is alkyl having 2 to 20 carbon atoms, R6 is alkyl, alkenyl, arylalkyl, arylalkenyl, heteroalkyl, heteroalkenyl, heteroarylalkyl, heteroarylalkenyl, or a heteryl group thereof having 2 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

R7 to R9 are each independently hydrogen; alkyl, alkenyl, arylalkyl, or arylalkenyl having 1 to 20 carbon atoms; cycloalkyl, cycloalkenyl, arylcycloalkyl, or arylcycloalkenyl having 3 to 20 carbon atoms; aryl having 6 to 20 carbon atoms; or alkylaryl having 7 to 20 carbon atoms.

In an embodiment, R7 to R9 of Formula 3 may be hydrogen.

In an embodiment, the transition metal compound may comprise an organic chromium compound, and the organic chromium compound may comprise at least one selected from the group consisting of chromium(III) acetyl acetonate, trichlorochromium tris tetrahydrofuran, chromium(III)-2-ethylhexanoate, chromium(III) tris (2,2,6,6-tetramethyl-3,5-heptanedionate), chromium(III) benzoyl acetonate, chromium(III) hexafluoro-2,4-pentanedionate and chromium (III) acetate hydroxide.

In an embodiment, the co-catalyst may be at least one selected from the compounds represented by the following Formulae 4 to 6.

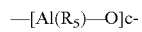 [Formula 4]

In the above Formula 4, each $R_5$ is the same or different and is independently a halogen radical, a hydrocarbyl radical having 1 to 20 carbon atoms, or a halogen substituted hydrocarbyl radical having 1 to 20 carbon atoms, and c is an integer of at least 2.

 [Formula 5]

In the above Formula 5, D is aluminum or boron, each $R_6$ is the same or different and is independently hydrogen, halogen, hydrocarbyl having 1 to 20 carbon atoms, or halogen substituted hydrocarbyl having 1 to 20 carbon atoms.

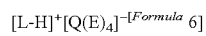 [Formula 6]

In the above Formula 6, L is a neutral Lewis base, $[L-H]^+$ is a brönsted acid, Q is boron or aluminum with an oxidation state of +3, and each E is independently aryl having 6 to 20 carbon atoms or alkyl having 1 to 20 carbon atoms, where at least one hydrogen atom is substituted with halogen, hydrocarbyl having 1 to 20 carbon atoms, an alkoxy functional group or a phenoxy functional group or unsubstituted.

According to another aspect of the present invention, there is provided a method for oligomerizing olefin comprising performing a multimerization reaction of olefin in a reaction temperature range of 30 to 150° C. in the presence of the oligomerization catalyst system prepared by the above-described method for preparing an oligomerization catalyst system.

In an embodiment, the reaction temperature may be in a range of 60 to 130° C.

In an embodiment, an activity of the catalyst system in a whole reaction temperature range may be 100,000 kg/molCr/hr or more in a batch type process, and 100,000 kg/molCr or more in a continuous type process.

In an embodiment, an activity decreasing ratio of the catalyst system according to temperature increase may be less than 6% in a whole reaction temperature range.

In an embodiment, selectivity of 1-hexene and 1-octene relative to a total amount of a product may be 80 wt % or more in a whole reaction temperature range.

Advantageous Effects

In the method for preparing an oligomerization catalyst system according to the present disclosure, an oligomerization catalyst system of which activity may not be deteriorated but maintained during an oligomerization reaction at a high temperature, may be provided by decreasing the contacting and aging temperature of a catalyst composition comprising a ligand compound and a transition metal compound, with a co-catalyst, and activating a catalyst system in a short time. Accordingly, the temperature range in the oligomerization reaction may be more freely controlled, and various processing merits may be attained.

MODE FOR CARRYING OUT THE INVENTION

Hereinafter, the present invention will be described in detail to assist the understanding of the present invention. The terms or words used in the present disclosure or claims should not be defined or interpreted in common or dictionary meaning, but should be interpreted as having a meaning that is consistent with their meaning in technical spirit of the present invention on the basis that the inventors may appropriately define the concept of the terms to explain the invention by their best way.

The terminology used herein is for the purpose of describing particular example embodiments only and is not intended to limit the present inventive concept. As used herein, the singular forms are intended to include the plural forms as well, unless the context clearly indicates otherwise.

It will be further understood that the terms "comprises", "comprising", etc. when used in this specification, specify the presence of stated features, numerals, steps, elements or the combination thereof, but do not preclude the presence or addition of one or more other features, numerals, steps, elements or the combination thereof.

In the present disclosure throughout, the terms "catalyst system" or "catalyst composition" means a state obtainable as a catalyst composition having activity by adding three components comprising a transition metal source, a ligand compound and a co-catalyst, or alternatively, two components having a transition metal compound and a co-catalyst simultaneously or in an optional order. The three components or the two components of the catalyst system may be added in the presence or non-presence of a solvent and a monomer, and the two terms may interchangeably be used.

The term "oligomerization" used in the present disclosure means the oligomerization of olefin. According to the number of the olefin, trimerization, or tetramerization may be referred to, and the general term thereof is multimerization. Particularly, in the present disclosure, the oligomerization means the selective preparation of 1-hexene and 1-octene which are main comonomers of LLDPE from ethylene.

In the present disclosure, a hydrocarbyl group means all compounds composed of only carbon and hydrogen, for example, alkyl, aryl, alkenyl, cycloalkyl, etc., and the hydrocarbyl group may mean both a linear chain and a branched chain unless otherwise referred to and may mean both unsubstituted and substituted type. For example, the alkyl having 1 to 20 carbon atoms may mean methyl, ethyl, propyl, isopropyl, butyl, isobutyl, pentyl, isopentyl, neopentyl, etc., and the aryl having 6 to 20 carbon atoms may mean, for example, phenyl, naphthyl, anthracenyl, etc., without limitation.

In the present disclosure, an alkylaryl group means aryl having at least one alkyl group as a substituent, and an arylalkyl group means alkyl having at least one aryl group as a substituent.

In the present disclosure, a heteroatom means N, O, S or P, and the heterohydrocarbyl may mean hydrocarbyl including at least one heteroatom. That is, the heteroalkyl may mean an alkyl of which one carbon is substituted with a heteroatom or may mean an alkyl comprising a heteroatom as a substituent. Heteroaryl group may mean an aromatic ring of which one carbon is substituted with a heteroatom such as pyridyl. In addition, the same may go for heteroarylakyl, heteroalkylaryl, heteroalkenylaryl, etc.

In the heterohydrocarbyl group, a linking point for functionalization is carbon, however, in "heteryl group" such as "hydrocarboheteryl group", "organoheteryl group", "heteryl group thereof", etc., the linking point for functionalization is a heteroatom.

Oligomerization Catalyst System and Method for Preparing the Same Method for Preparing Oligomerization Catalyst System According to an embodiment of the present disclosure, a method for preparing an oligomerization catalyst system comprising preparing a catalyst composition by mixing a ligand compound comprising a diphosphine moiety represented by the following Formula 1 and a transition metal compound; and mixing and activating a co-catalyst and the catalyst composition at a temperature from −40 to 80° C., is provided.

[Formula 1]

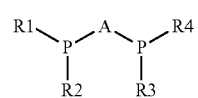

In Formula 1, A is N, As or Sb, R1 to R4 are each independently hydrocarbyl, heterocarbyl or hydrocarbylheteryl having 1 to 20 carbon atoms.

Particular explanation on the ligand compound, the transition metal compound and the co-catalyst is as follows.

The catalyst composition comprises a ligand compound and a transition metal compound, and in the method for preparing the oligomerization catalyst system according to the present disclosure, the ligand compound and the transition metal compound may be mixed in advance to induce a metalation reaction between the two compounds.

The metalation reaction may be a reaction for making a coordination bond between the ligand compound and the transition metal compound, and the coordination state of the ligand compound and the transition metal compound, the activation point of the ligand compound, etc. will be explained below.

After a catalyst composition is prepared via a sufficient metalation reaction of the ligand compound and the transition metal compound, the catalyst composition and a co-catalyst are mixed and activated. The activation may mean activation as an oligomerization catalyst system via the contact and aging of the catalyst composition and the co-catalyst.

The activation of the catalyst composition and the co-catalyst may be performed at a temperature from −40 to 80° C., preferably, from 20 to 80° C. or from 25 to 60° C. In the case that the contact and aging of the catalyst composition and the co-catalyst for activation is performed at a high temperature greater than 80° C., the ligand and the transition metal of the catalyst composition may be excessively activated by a metal alkyl possibly used as the co-catalyst, and a side reaction may be generated during an oligomerization reaction or the activity may be deteriorated at an early stage.

In addition, in the case that the contact and aging of the catalyst composition and the co-catalyst for activation is performed at an extremely low temperature less than −40°

C., energy necessary for the activation of the catalyst may not be supplied, and the catalyst may not be activated.

The activation of the catalyst composition and the co-catalyst may be performed by contacting the co-catalyst and the catalyst composition present as a liquid phase after being mixed with an organic solvent, and aging for a certain time period. The activation may be performed by stirring, simple mixing, etc., without specific limitation, and any method for generating the activity as the oligomerization catalyst system via the contact of the catalyst composition and the co-catalyst may be applied.

The organic solvent may comprise, for example, heptane, toluene, cyclohexane, methylcyclohexane, 1-hexene, diethyl ether, tetrahydrofuran, acetonitrile, dichloromethane, chloroform, chlorobenzene, methanol, acetone, etc., without limitation.

For example, in the case that time necessary from an initial contact point of the co-catalyst with the catalyst composition (the temperature at this point is referred to as "temperature a") to a point just before the contact with a reactant (for example, ethylene) is set to time A, and time necessary for elevating the temperature of a mixture of the catalyst composition, the co-catalyst and the reactant to an oligomerization temperature (the reaction temperature is referred to as "temperature b") is set to time B, the activation time of the co-catalyst and the catalyst composition may mean the sum of time A and time B, or in the case that the initial point of time A and the initial point of time B are different, and firstly initiated time is firstly over, may mean time consumed from the initial point of the firstly initiated time to the end point of a subsequently initiated time. Alternatively, in the case where one time is included in another time consumed for a longer period (for example, in the case that time A is completely included in time B, or time B is completely included in time A), the activation time may mean longer time.

The activation of the catalyst composition and the co-catalyst may be performed within five minutes, and preferably, in three minutes. In the case that the contact and aging time of the catalyst composition and the co-catalyst for the activation is greater than five minutes, the over-activation of the oligomerization catalyst system may occur as in the case that the activation is performed at a high temperature, and the time may preferably be within five minutes.

In the method for preparing an oligomerization catalyst system according to an embodiment of the present disclosure, when the activation is attained at a low temperature in a short time as the activation conditions of the catalyst composition and the co-catalyst, the coordination bond of the ligand compound and the transition metal compound of the oligomerization catalyst system may be stabilized, and the thermostability of the catalyst system may increase. In this case, even though an oligomerization reaction is performed at a high temperature (from about 60° C. to about 120° C.), the catalyst system has high structural durability and little changes of physical properties, and the activity of the catalyst system may be continuously maintained.

The activity of the catalyst system manufactured in the above-described activation conditions may be about 100,000 kg/molCr/hr or more in a batch type process, preferably, may be 120,000 kg/molCr/hr or more, and more preferably, 150,000 kg/molCr/hr or more. In addition, the activity of the catalyst system may be about 100,000 kg/molCr or more in a continuous type process, preferably, 120,000 kg/molCr or more, and more preferably, 150,000 kg/molCr or more.

The activity of the catalyst system may not be deteriorated but maintained at a high temperature as described above, and an activation deterioration ratio according to the increase of the oligomerization reaction temperature may be less than 6%. In this case, the oligomerization reaction temperature may be in a range of 30 to 150° C., 60 to 130° C., or 70 to 110° C.

Meanwhile, generally, in the case where an oligomerization process is a batch type process, the co-catalyst may be mixed in an organic solvent phase and injected to a reactor, and the catalyst composition may be injected together with olefin which is a reactant, directly injected to the reactor, or injected to a line for injecting the co-catalyst and injected to the reactor. In addition, in the case where the oligomerization process is a continuous type process, the co-catalyst and the catalyst composition may be injected to the reactor via separate lines, and the reactant may be also injected via a separate line to the reactor. Accordingly, with the decrease of contact time with the reactor, the activity may be possibly maintained at a high temperature.

In the oligomerization catalyst system, the molar ratio of the ligand compound:transition metal compound:co-catalyst may be from about 0.5:1:1 to about 10:1:10,000, and preferably, from about 0.5:1:100 to about 5:1:3,000 to increase selectivity to linear alpha olefins and the activity of a multimerization reaction. However, an example of the oligomerization catalyst system according to the present disclosure is not limited thereto.

Ligand Compound

A PNP-based ligand compound may be applied to the method for preparing an oligomerization catalyst system according to an embodiment of the present disclosure, without specific limitation, however even better effects may be obtained when the following ligand compound is applied.

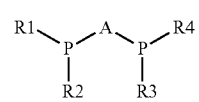

[Formula 1]

In Formula 1, A is N, As or Sb, and R1 to R4 are each independently aryl having 6 to 20 carbon atoms or alkylaryl having 7 to 20 carbon atoms.

In addition, the ligand compound comprising a diphosphine moiety represented by Formula 1 may comprise at least two diphosphine moieties represented by the following Formula 2.

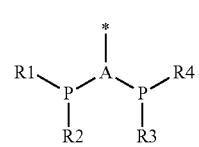

[Formula 2]

In the above Formula 2, A and R1 to R4 are the same as defined in Formula 1, and * is a linker connecting at least two diphosphine moieties.

Further, in the case that the number of the diphosphine moiety represented by the above Formula 2 is two, and A is nitrogen (N), the ligand compound may include a compound represented by the following Formula 2a.

[Formula 2a]

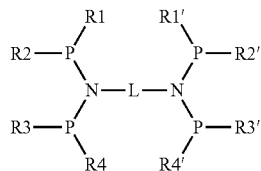

In the above Formula 2a, each of R1 to R4 and R1' to R4' may be selected from the same group of R1 to R4 in Formula 2, and L may be a linker connecting two diphosphine moieties.

The linker L connecting at least two diphosphine moieties may be a hydrocarbyl group having various structures, and the carbon number between the diphosphine moieties for the shortest distance may be from 2 to 30. That is, the hydrocarbyl group is provided for the connection between two or more diphosphine moieties, and the carbon number in the hydrocarbyl group for connecting the diphosphine moieties with the shortest distance may be in a range from 2 to 8.

Particularly, the hydrocarbyl linker may be combined with at least one group selected from the group consisting of an aliphatic group having 2 to 20 carbon atoms, a hetero aliphatic group having 2 to 20 carbon atoms, an alicyclic group having 3 to 20 carbon atoms, a hetero alicyclic group having 3 to 20 carbon atoms, an aromatic group having 6 to 20 carbon atoms, and a hetero aromatic group having 6 to 20 carbon atoms, and may have any structure, without specific limitation only if satisfying the above conditions.

Non-limiting examples of the linker L for connecting at least two groups represented by the above Formula 1 via 2 to 30 carbon atoms may be a compound comprising an aliphatic group having 2 to 20 carbon atoms (for example, an alkylene group, an alkenylene group, an alkynylene group, or a hetero aliphatic group comprising a heteroatom in the aliphatic group), an alicyclic group having 2 to 20 carbon atoms (for example, a cycloalkylene group, a cycloalkenylene group, a cycloalkynylene group, or a hetero alicyclic group comprising a heteroatom in the alicyclic group), or a combined group of the aliphatic (or hetero aliphatic) group and the alicyclic (or hetero alicyclic) group.

Non-limiting examples of the linker may comprise a hydrocarbyl group represented by the following structures. In the following examples, the diphosphine moiety represented by the above Formula 1 is designated by [A], [A'] or [A"] for convenience, and [A], [A'] or [A"] may be the same or different according to the group selected for R1 to R4.

(i) a compound having a group connecting a plurality of As via two or three carbon atoms:

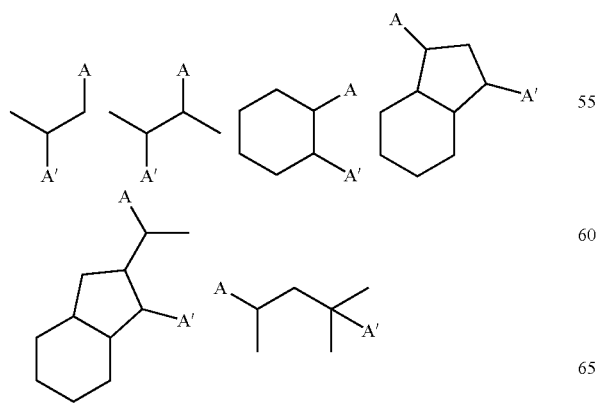

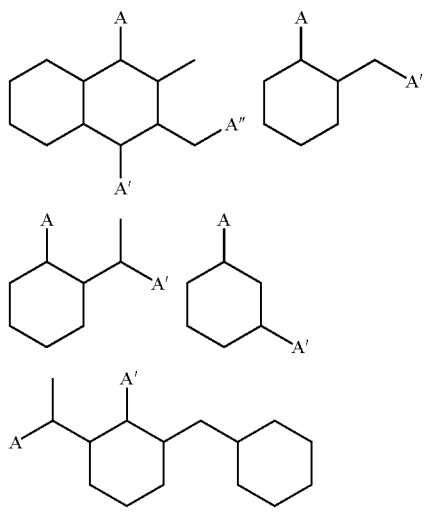

(ii) a compound having a group connecting a plurality of As via four carbon atoms:

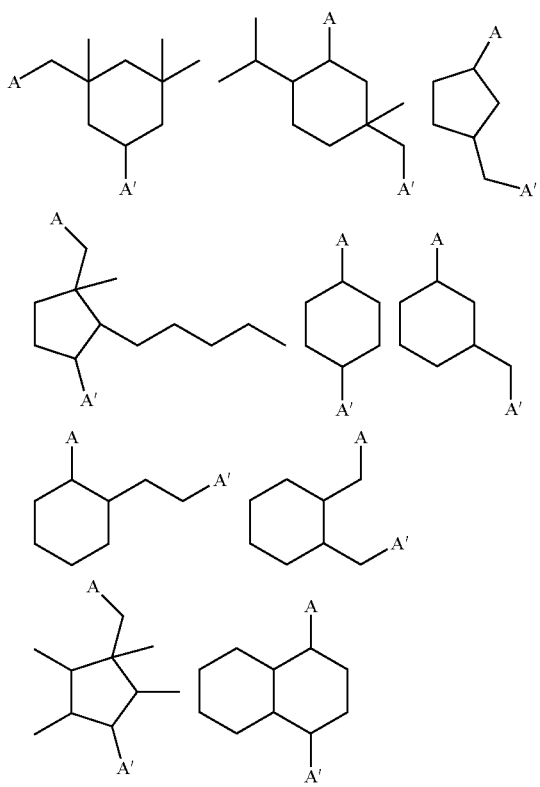

(iii) a compound having a group connecting a plurality of As via five carbon atoms:

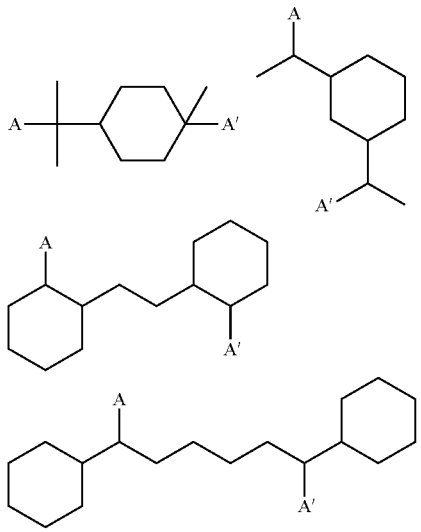

As described above, in the case that at least two diphosphine moieties represented by Formula 1 are connected via four carbon atoms, a connecting group via four carbon atoms may preferably comprise a flexible aliphatic group for favorable interaction between chromium complexes of the at least two diphosphine moieties.

That is, even though at least two diphosphine moieties represented by Formula 1 are connected via four carbon atoms, in the case that the diphosphine moieties are connected via a group not comprising an aliphatic group but only including an alicyclic group or an aromatic group such as cyclohexane at positions 1 and 4, interaction may be extremely limited. Accordingly, activity per unit PNP—Cr may be largely decreased, and selectivity for alpha-olefins having a small carbon number such as 1-hexene and 1-octene may be deteriorated.

Meanwhile, the ligand compound represented by Formula or 2a may be synthesized by the following Reaction 1, without limitation.

[Reaction 1]

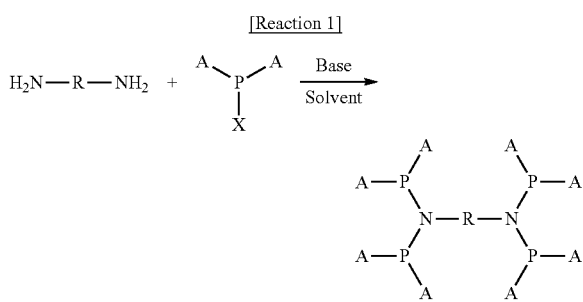

In the above Reaction 1, each A is independently the same or different from each other and is the same as defined for R1 to R4 in Formula 1, 2 or 2a, R is a linker connecting via 2 to 8 carbon atoms and the same as defined in Formula 2 or 2a, and X is halogen.

According to another embodiment of the present disclosure, the ligand compound may comprise a compound represented by the following Formula 3.

[Formula 3]

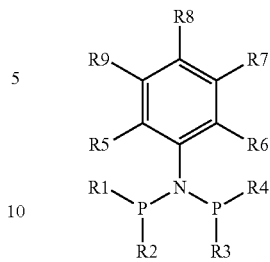

In Formula 3, R1 to R4 are each independently aryl having 6 to 20 carbon atoms or alkylaryl having 7 to 20 carbon atoms, and R5 is alkyl having 1 to 20 carbon atoms.

In the case that R5 is methyl, R6 may be a linear group of alkyl, alkenyl, heteroalkyl, heteroalkenyl, or a heteryl group thereof having 2 or 3 carbon atoms; alkyl, alkenyl, arylalkyl, arylalkenyl, heteroalkyl, heteroalkenyl, heteroarylalkyl, heteroarylalkenyl, or a heteryl group thereof having 4 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

In addition, in the case that R5 is methyl, R6 may preferably be heteroalkyl, heteroalkenyl, heteroarylalkyl, heteroarylalkenyl, or a heteryl group thereof having 2 to 20 carbon atoms; heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

In the case that R5 is alkyl having 2 to 20 carbon atoms, R6 may be alkyl, alkenyl, arylalkyl, arylalkenyl, heteroalkyl, heteroalkenyl, heteroarylalkyl, heteroarylalkenyl, or a heteryl group thereof having 2 to 20 carbon atoms; cycloalkyl, cycloalkenyl, arylcycloalkyl, arylcycloalkenyl, heterocycloalkyl, heterocycloalkenyl, heteroarylcycloalkyl, heteroarylcycloalkenyl, or a heteryl group thereof having 3 to 20 carbon atoms; aryl, heteroaryl, or a heteryl group thereof having 6 to 20 carbon atoms; or alkylaryl, heteroalkylaryl, or a heteryl group thereof having 7 to 20 carbon atoms.

R7 to R9 may be each independently hydrogen; alkyl, alkenyl, arylalkyl, or arylalkenyl having 1 to 20 carbon atoms; cycloalkyl, cycloalkenyl, arylcycloalkyl, or arylcycloalkenyl having 3 to 20 carbon atoms; aryl having 6 to 20 carbon atoms; or alkylaryl having 7 to 20 carbon atoms.

As described above, the ligand compound represented by Formula 3 may be, for example, a compound obtained by substituting at carbon atoms of positions 2 and 6 in an aniline compound with R5 and R6, and the properties of the ligand compound and the oligomerization catalyst system comprising the same may be changed according to the substituent at the carbon atoms of positions 2 and 6.

In the case where a methyl group is substituted at the carbon atom of position 2, a group different from the substituent at position 2 may be substituted at the carbon atom of position 6 to attain an asymmetric structure.

As non-limiting examples, a linear group of an alkyl group, an alkenyl group, a heteroalkyl group, a heteroalkenyl group, or the heteryl group thereof having 2 or 3 carbon atoms may be substituted; or an alkyl group, an alkenyl group, an arylalkyl group, an arylalkenyl group, a heteroalkyl group, a heteroalkenyl group, a heteroarylalkyl group, a heteroarylalkenyl group, or the heteryl group thereof having 4 to 20 carbon atoms may be substituted.

In addition, a cycloalkyl group, a cycloalkenyl group, an arylcycloalkyl group, an arylcycloalkenyl group, a heterocycloalkyl group, a heterocycloalkenyl group, a heteroarylcycloalkyl group, a heteroarylcycloalkenyl group, or the heteryl group thereof having 3 to 20 carbon atoms may be substituted; an aryl group, a heteroaryl group, or the heteryl group thereof having 6 to 20 carbon atoms may be substituted; or an alkylaryl group, a heteroalkylaryl group, or the heteryl group thereof having 7 to 20 carbon atoms may be substituted.

In addition, in the case where an alkyl group having 2 to 20 carbon atoms is substituted at the carbon atom of position 2, a substituent same as or different from the substituent at position 2 may be substituted at the carbon atom of position 6.

As non-limiting examples, an alkyl group, an alkenyl group, an arylalkyl group, an arylalkenyl group, a heteroalkyl group, a heteroalkenyl group, a heteroarylalkyl group, a heteroarylalkenyl group, or the heteryl group thereof having 2 to 20 carbon atoms may be substituted; a cycloalkyl group, a cycloalkenyl group, an arylcycloalkyl group, an arylcycloalkenyl group, a heterocycloalkyl group, a heterocycloalkenyl group, a heteroarylcycloalkyl group, a heteroarylcycloalkenyl group, or the heteryl group thereof having 3 to 20 carbon atoms may be substituted; an aryl group, a heteroaryl group, or the heteryl group thereof having 6 to 20 carbon atoms may be substituted; or an alkylaryl group, a heteroalkylaryl group, or the heteryl group thereof having 7 to 20 carbon atoms may be substituted.

Due to the structural characteristics of the substituent groups for the aniline group, in the catalyst system comprising the ligand compound, PNP—Cr may easily interact according to various conditions such as electronic or steric circumstances around a transition metal, and the high activity of an oligomerization reaction may be illustrated. Further, high selectivity particularly for 1-hexene, 1-octene, etc. may be illustrated, and the amount of an 1-hexene isomer which may induce large affects to a product during oligomerizing may be largely decreased. Wherein, 1-hexene isomer has a large affects to a product even in small amounts during oligomerizing. Accordingly and incidentally, energy may be saved, because a separating process may become unnecessary according to the increase of 1-hexene and the decrease of 1-hexene isomer.

The ligand compound may be synthesized by the following Reaction 2, without limitation.

[Reaction 2]

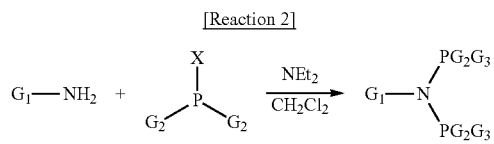

In the above Reaction 2, G1 may be a phenyl group having R5 to R9 in Formula 3, each of G2 and G3 may be R1 to R4 in Formula 3, and X may be halogen.

Reaction 2 is a general reaction for synthesizing a ligand compound represented by Formula 3 and may be a reaction for producing diphosphinoamine via the reaction of an amine and phosphine. That is, in the reaction, the amine as a nucleophile may push a leaving group represented by X in the phosphine for substitution. X may be any functional group which may be easily separated and stabilized, without limitation. Typically, halogens such as Cl, Br or I may be used.

Ligand Compound and Transition Metal Compound

Such a selective olefin oligomerization reaction is closely concerned with a catalyst system used. The catalyst system used for the oligomerization reaction of olefin comprises a transition metal compound functioning as a main catalyst and a co-catalyst. In this case, according to the chemical structure of the ligand, the structure of an active catalyst may be changed, and so, olefin selectivity, activity or the amount of by-products may be changed.

The transition metal compound in the oligomerization catalyst system according to an embodiment of the present disclosure acts as a main catalyst and may have a state making a coordination bond with the ligand compound as described above.

Particularly, the transition metal and the ligand compound comprising at least two diphosphine moieties represented by the above Formula 2 may make a coordination bond as represented in the following Formula 2-1.

[Formula 2-1]

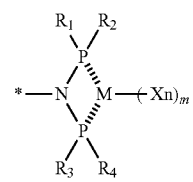

In the above Formula 2-1, R1 to R4 are the same as defined in Formula 1 and * is the same as defined in Formula 2, M may be a transition metal, and preferably, Cr, Xn may be H, F, Cl, Br, I, alkyl, alkenyl, arylalkyl, heteroalkyl, heteroalkenyl or heteroarylalkyl having 1 to 6 carbon atoms, halogen, acetate, or acetyl acetonate, and m is an oxidation number of M and may be a natural number.

In addition, the transition metal compound and the ligand compound represented by Formula 2a may make a coordination bond as shown in the following Formula 2a-1.

[Formula 2a-1]

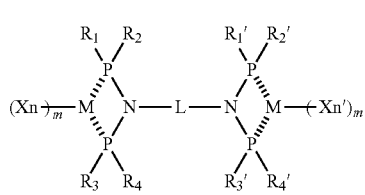

In Formula 2a-1, R1 to R4, Xn, m and M are the same as defined in Formula 2-1, and R1' to R4' and Xn' are also the same as R1 to R4 and X1 to X3.

In addition, the transition metal compound and the ligand compound represented by Formula 3 may make a coordination bond as shown in the following Formula 3-1.

[Formula 3-1]

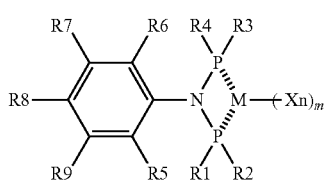

In Formula 3-1, Xn, m and M are the same as defined in Formula 2-1, and R1 to R9 are the same as defined in Formula 3.

Particularly, the transition metal compound may comprise an organochromium compound, and the organochromium compound may be at least one selected from the group consisting of chromium(III)acetylacetonate, trichlorochromiumtristetrahydrofuran, chromium(III)-2-ethylhexanoate, chromium(III)tris(2,2,6,6-tetramethyl-3,5-heptanedionate), chromium(III)benzoylacetonate, chromium(III)hexafluoro-2,4-pentanedionate and chromium(III)acetatehydroxide.

Co-Catalyst

The co-catalyst is an organometallic compound comprising a metal in group 13 and may be generally any one which may be used for multimerizing olefin in the presence of a transition metal compound catalyst, without specific limitation. Particularly, the co-catalyst may be at least one selected from the group consisting of the compounds represented by the following Formulae 4 to 6.

—[Al($R_5$)—O]c- [Formula 4]

In the above Formula 4, each $R_5$ is the same or different from each other and is independently a halogen radical, a hydrocarbyl radical having 1 to 20 carbon atoms, or a halogen substituted hydrocarbyl radical having 1 to 20 carbon atoms, and c is an integer of at least 2.

D($R_6$)$_3$ [Formula 5]

In the above Formula 5, D is aluminum or boron, each $R_6$ is the same or different from each other and is independently hydrogen or halogen, a hydrocarbyl having 1 to 20 carbon atoms, or halogen substituted hydrocarbyl having 1 to 20 carbon atoms.

[L-H]$^+$[Q(E)$_4$]$^-$ [Formula 6]

In the above Formula 6, L is a neutral Lewis base, [L-H]$^+$ is a brönsted acid, Q is boron or aluminum with an oxidation state of +3, and each E is independently aryl having 6 to 20 carbon atoms or alkyl having 1 to 20 carbon atoms, where at least one hydrogen atom is substituted with halogen, hydrocarbyl having 1 to 20 carbon atoms, an alkoxy functional group or a phenoxy functional group or unsubstituted.

The compound represented by Formula 4 may be modified methyl aluminoxane (MAO), methyl aluminoxane (MAO), ethyl aluminoxane, isobutyl aluminoxane, butyl aluminoxane, etc.

The alkyl metal compound represented by the above Formula 5 may comprise, for example, trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc.

Examples of the compound represented by the above Formula 6 comprises, for example, triethylammoniumtetraphenylboron, tributylammoniumtetraphenylboron, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentafluorophenylaluminum, triphenylphosphoniumtetraphenylaluminum, trimethylphosphoniumtetraphenylaluminum, triphenylcarboniumtetraphenylboron, triphenylcarboniumtetraphenylaluminum, triphenylcarboniumtetra(p-trifluoromethylphenyl)boron, triphenylcarboniumtetrapentafluorophenylboron, etc.

The co-catalyst of the oligomerization catalyst system according to an embodiment may preferably comprise aluminoxane, and more preferably, methyl aluminoxane (MAO) or modified methyl aluminoxane (MMAO) may be used.

According to another embodiment of the present disclosure, an oligomerization catalyst system prepared via the above-described method is provided.

The catalyst system may maintain activity in the case that the reaction temperature of an oligomerization reaction is 60° C. or more, further at the reaction temperature of 30 to 150° C. Accordingly, the temperature of the oligomerization reaction in the presence of the oligomerization catalyst system may be more freely controlled. 1-hexene and 1-octene may be prepared by applying various methods in the oligomerization, and other diverse merits may be attained.

Method for Oligomerizing Olefin

According to another embodiment of the present disclosure, a method for preparing olefin oligomer comprising a step of performing olefin multimerization reaction in the presence of the oligomerization catalyst system may be provided. By using the olefin oligomerization catalyst system according to an embodiment, a method for oligomerizing olefin having improved activity and selectivity of a reaction may be provided. In this case, the olefin may include ethylene.

Non-limiting examples of the oligomerization method of the olefin may comprise a multimerization reaction of olefin by controlling the reaction temperature in a range of 30 to 150° C. in the presence of the oligomerization catalyst system comprising the ligand compound, the transition metal compound the co-catalyst so that the molar ratio of 1-hexene and 1-octene in a product comprising 1-hexen and 1-octene becomes a predetermined value, wherein the predetermined value of the molar ratio of 1-hexene and 1-octene may be selected from a range of 1:0.5 to 1:7.

In a conventional oligomerization method, in order to obtain 1-hexene and 1-octene, which are main products, to desired ratios at the same time, two kinds of appropriate catalysts for producing each compound are mixed to control the production ratio of two kinds of alpha olefins.

However, the method for oligomerizing olefin according to an embodiment of the present disclosure is a method of controlling the ratio of the alpha olefins which are main products and may produce 1-hexene and 1-octene in a desired ratio by selecting the method of controlling the reaction temperature and controlling the reaction temperature thereby. Accordingly, 1-hexene and 1-octene may be easily obtained in a desired ratio by controlling only the reaction temperature, thereby markedly improving the convenience and/or economic feasibility of a process.

Particularly, the controlling range of the reaction temperature may be from 30 to 150° C., from 60 to 130° C., or from 70 to 110° C. By controlling the reaction temperature to the temperature range, the desired ratio of 1-hexene and 1-octene may be determined prior to the oligomerization reaction, and 1-hexene and 1-octene with a predetermined value may be obtained. In this case, the weight ratio of 1-hexene and 1-octene may be predetermined to a range of 1:0.5 to 1:7, or 1:0.9 to 1:6.6.

In addition, in the case that the reaction temperature is from 50 to 60° C., the weight ratio of 1-hexene and 1-octene may be from about 1:2 to 1:7, and preferably, from 1:3 to 1:7. In the case that the reaction temperature is controlled to about 50 to 60° C., the production amount of 1-octene may be greater than that of 1-hexene. In the case that the reaction temperature is further increased, the ratio of 1-hexene may be further increased, and even though the reaction temperature is greater than 80° C., the activity of the catalyst system may be maintained. The production ratio of 1-hexene and 1-octene may be controlled by only controlling the temperature up to about 150° C.

That is, by using the catalyst system according to the present disclosure, the activity of the catalyst system may be maintained in an extensive temperature range, particularly, at a high temperature, and the ratio of 1-hexene and 1-octene may be controlled in a wide temperature range such as from 30 to 150° C. Accordingly, a linear alpha olefin mixture product having more diverse weight ratios may be prepared, and since the catalyst system maintains the activity in such a temperature range, the total amount of 1-hexene and 1-octene (that is, the selectivity of linear alpha olefins) may be maintained.

In addition, since the activity of the catalyst system is maintained in such a wide temperature range, the selectivity relative to the total amount of the product of 1-hexene and 1-octene may be maintained to 80 wt % or more in a whole reaction temperature range.

The application of the method of controlling the production ratio of 1-hexene and 1-octene by controlling the reaction temperature, to a method for oligomerizing olefin may be diverse, and practical application examples are as follows.

First, resultant values on the weight ratio of 1-hexene and 1-octene produced depending on the reaction temperature are obtained by repeating experiments, data on the average ratio of 1-hexene and 1-octene produced at a specific reaction temperature are classified, and a library is established from the classified data. For the mass production of alpha olefins, the temperature of a multimerization reaction is controlled using the library established in advance via repeated experiments, and the predetermined production ratio of 1-hexene and 1-octene may be obtained as a desired value according to various conditions such as demand.

In addition, different from the process performed after establishing the library, a method of changing the reaction temperature from time to time after observing the ratio of 1-hexene and 1-octene produced during a process to a desired direction may be applied. Since the production ratio of 1-hexene tends to increase according to the increase of the multimerization reaction temperature, the above-described method may be practically applied for the change of the production ratio of 1-hexene and 1-octene according to the control of the reaction temperature.

The method of controlling the reaction temperature for controlling the ratio of 1-hexene and 1-octene may be applied to the method for oligomerizing olefin according to the present disclosure, and a practical application is not limited to the above-described two methods.

The method for preparing olefin oligomer comprising the multimerization reaction of olefin in the presence of the oligomerization catalyst system uses a catalyst system for oligomerizing olefin, and a method for oligomerizing olefin having improved activity and selectivity of a reaction may be provided. In this case, the olefin may comprise ethylene.

The method for oligomerizing olefin according to the present disclosure may preferably be a homogeneous liquid phase reaction using an oligomerization catalyst system, a common apparatus and contacting technique in the presence or non-presence of an inert solvent, a slurry reaction in which a catalyst system is partially or wholly undissolved, a two phase liquid/liquid reaction, or a bulk phase reaction or a gas phase reaction in which an olefin product acts as a main medium. The homogeneous liquid phase reaction is preferable.

The oligomerization method of olefin may be performed in an optional inert solvent which does not react with a catalyst compound and an activator. Appropriate inert solvents may comprise benzene, toluene, xylene, cumene, heptane, cyclohexane, methylcyclohexane, methylcyclopentane, hexane, pentane, butane, isobutene, etc., without limitation. In this case, the solvent may be used after removing a small amount of water or air acting as a catalyst poison by treating using a small amount of alkyl aluminum.

The oligomerization reaction of olefin may be performed under a pressure from about 1 bar to about 300 bar, and preferably, from about 2 bar to about 150 bar.

The pressure conditions may be optimized conditions for the multimerization reaction of olefin, and by multimerizing olefin in the above pressure range, selectivity to desired alpha-olefins may be good, the amount of by-products may decrease, process operating efficiency may be increased, and costs may be saved.

EXAMPLES

Hereinafter, examples of the present invention will be explained in detail so that a person skilled in the art may easily perform. However, the present invention may be embodied in various modifications and is not limited to the examples herein.

<Synthesis of Ligand Compound>

All reactions were performed under an argon atmosphere using Schlenk technique or a glove box. The ligand synthesized was analyzed after taking $^1$H (500 MHz) and $^{31}$P (202 MHz) NMR spectra using a Varian 500 MHz spectrometer.

Chemical shift values were represented by ppm downfield from TMS with a residual solvent peak as a reference. A phosphorous probe was calibrated using aqueous $H_3PO_4$.

Preparation Example

Under an argon atmosphere, 2-ethyl-6-methylaniline (5 mmol) and triethylamine (3-10 eq. to amine) were dissolved in dichloromethane (80 ml). With a flask in a water bath, chloroditolylphosphine (20 mmol, 2 eq. to amine) was slowly added and stirred overnight. After evaporating solvents in vacuum, THF was added and sufficiently stirred. A triethylammonium chloride salt was removed using an air-free glass filter. Solvents were removed from the filtrate to obtain a product.

<Preparation of Alpha-Olefin Oligomer>

Example 1

Preparation of Oligomerization Catalyst System

Under an argon gas atmosphere, $Cr(acac)_3$ (17.5 mg, 0.014 mmol) and a ligand compound (1.1 eq. to Cr) prepared according to the preparation method were added to a flask, and 100 ml of methylcyclohexane was added thereto, followed by stirring to obtain a 0.5 mM (to Cr) catalyst composition.

Then, 32 ml of MMAO (8.6 wt %, isoheptane solution) (Al/Cr=1,200) and 100 ml of the 0.5 ml catalyst composition were premixed in a round-bottomed flask at 25° C. for 2 minutes to prepare an oligomerization catalyst system.

Oligomerization of Olefin

A parr reactor having a volume of 600 ml was prepared and a vacuum state was made at 180° C. for 2 hours. Then, the inner portion was substituted with argon, and the temperature was decreased to the reaction temperature of 60° C. 140 g of methylcyclohexane was injected to the reactor, and 6.6 ml (2.5 μmol) of the premixed solution (oligomerization catalyst system) was injected to the reactor. Immediately after the injection, the valve of an ethylene line adjusted to 60 bar was opened to fill up the inner portion of the reactor with ethylene, followed by stirring at the reaction temperature of 60° C. in 500 rpm for 15 minutes.

The valve of an ethylene line was closed, and the reactor was cooled to 0° C. using a dry ice/acetone bath, unreacted ethylene was slowly ventilated, and 1 ml of nonane (GC internal standard) was injected. After that, a small amount of the liquid portion of the reactor was collected and quenched with water. An organic layer was filtered using a PTFE syringe filter, and GC analysis was conducted.

400 ml of ethanol/HCl (10 vol %) was added to the remaining reaction product, followed by stirring and filtering to obtain a polymer. The polymer thus obtained was dried at 60° C. in a vacuum oven overnight, and the weight was measured.

Example 2

The preparation of a catalyst system, oligomerization, GC analysis and the measurement of the weight of the polymer thus obtained were performed according to the same method described in Example 1 except for setting the activation temperature to 60° C. during premixing for preparing the oligomerization catalyst system.

Example 3

The preparation of a catalyst system, oligomerization, GC analysis and the measurement of the weight of the polymer thus obtained were performed according to the same method described in Example 1 except for setting the oligomerization reaction temperature to 80° C.

Example 4

The preparation of a catalyst system, oligomerization, GC analysis and the measurement of the weight of the polymer thus obtained were performed according to the same method described in Example 1 except for setting the activation temperature to 80° C. and the reaction temperature of oligomerization to 80° C. during premixing for preparing the oligomerization catalyst system.

Comparative Examples 1 to 4

The preparation of a catalyst system, oligomerization, GC analysis and the measurement of the weight of the polymers thus obtained were performed according to the same method described in Example 1 except for setting the mixing time and activation temperature during premixing for preparing the oligomerization catalyst system and the oligomerization temperature as in the following Table 1.

Evaluation Results

The results of the examples and the comparative examples are shown in the following Table 1.

TABLE 1

| | Premixing | | Reaction | | | | | 1-C6 + |
|---|---|---|---|---|---|---|---|---|
| | Temperature (° C.) | Time (min) | temperature ° C. | ΔT ° C. | Activity ton/molCr/hr | 1-C6 % | 1-C8 % | 1-C8 % |
| Example 1 | 25 | 2 | 60 | 40 | 182 | 41.8 | 43.6 | 90.6 |
| Example 2 | 60 | 2 | 60 | 13 | 175 | 47.3 | 42.0 | 89.3 |
| Example 3 | 25 | 2 | 80 | 15 | 174 | 47.1 | 43.6 | 90.6 |
| Example 4 | 80 | 2 | 80 | 13 | 157 | 47.0 | 43.3 | 90.3 |
| Comparative Example 1 | 25 | 100 | 60 | 4 | 50 | 24.1 | 65.4 | 89.5 |
| Comparative Example 2 | 25 | 5 | 80 | 0 | 42 | 30.3 | 54.6 | 85.0 |
| Comparative Example 3 | 80 | 5 | 80 | 4 | 44 | 40.3 | 50.0 | 90.3 |
| Comparative Example 4 | 80 | 100 | 80 | 0 | 0 | 0 | 0 | 0 |

Referring to Table 1, the activity of the catalyst systems obtained in Examples 1 to 4 by aging the co-catalyst and the catalyst composition at the temperature of −40 to 80° C. with an aging time of less than 5 minutes, was markedly better when compared to those of Comparative examples 1 to 4 obtained by aging for 5 minutes or more. That is, the activating conditions of the catalyst composition and the co-catalyst comprised the aging temperature of −40 to 80° C. with the short aging time of less than 5 minutes.

Example 5: Continuous Type Process

Under a nitrogen gas atmosphere, cyclohexane and ethylene were continuously injected with the flow rate of 1.2 kg/hr and 1.75 kg/hr to a 2 L CSTR reactor, and the pressure was maintained to 60 bar. To a 10 L pressurized vessel, the ligand prepared in the preparation example and Cr(acac)$_3$ in a molar ratio of 0.55:1 were injected, and a catalyst solution diluted in cyclohexane to 0.05 M was injected with a rate of 5.8 ml/min. At the same time, a solution of MMAO co-catalyst diluted in cyclohexane was continuously injected in line with the amount injected of the catalyst solution so that the molar ratio of Al:Cr is 1200:1. The reaction temperature was controlled to 60° C. by continuously injecting water at room temperature to a reactor jacket. During performing a stable reaction for 2 hours, a reaction product drained was collected for 1 hour and 5 ml thereof was taken and quenched with water. An organic layer was filtered using a PTFE syringe filter, GC analysis was conducted, and the results are shown in the following Table 2.

TABLE 2

|  | Activity kg/molCr | 1-C6 wt % | 1-C8 wt % | 1-C6 + 1-C8 wt % | 1-C10 to 1-C40 wt % | C6 isomer wt % |
|---|---|---|---|---|---|---|
| Example 5 | 128,900 | 32.5 | 53.4 | 85.8 | 11.6 | 1.8 |

Referring to Table 2, good activity of a catalyst system may be obtained even though applying the activation step of a catalyst system according to the present disclosure to a continuous process as in Example 5, like in the batch type process of Examples 1 to 4. Accordingly, the activity of the catalyst system may be good as in the batch type process, and the selectivity of linear alpha olefins may be also good.

Examples 6 to 10

(Step 1)
Under an argon gas atmosphere, Cr(acac)$_3$ (17.5 mg, 0.014 mmol) and the ligand compound (1.1 eq. to Cr) prepared in the preparation example were added to a flask, and 100 ml of methylcyclohexane was added thereto, followed by stirring to obtain a 0.5 mM (to Cr) solution.

(Step 2)
A parr reactor having a volume of 600 ml was prepared and a vacuum state was made at 180° C. for 2 hours. Then, the inner portion of the reactor was replaced with argon, and the temperature was decreased to 60° C. After that, 140 g of methylcyclohexane and 1.6 ml of MMAO (8.6 wt %, isoheptane solution) (Al/Cr=1,200) were injected, and 5 ml of the 0.5 mM solution (2.5 μmol) was injected to the reactor. The valve of an ethylene line adjusted to 60 bar was opened to fill up the reactor with ethylene, followed by stirring in 500 rpm at a temperature range of 70 to 110° C. while changing the temperature by 10° C. unit (each for Examples 6 to 10) for 15 minutes at each temperature.

The valve of an ethylene line was closed, and the reactor was cooled to 0° C. using a dry ice/acetone bath, unreacted ethylene was slowly ventilated, and 1 ml of nonane (GC internal standard) was injected. After that, a small amount of the liquid portion of the reactor was collected and quenched with water. An organic layer was filtered using a PTFE syringe filter, and GC analysis was conducted.

(Step 3)
400 ml of ethanol/HCl (10 vol %) was added to the remaining reaction product, followed by stirring and filtering to obtain a polymer. The polymer thus obtained was dried at 60° C. in a vacuum oven overnight, and the weight was measured.

Experimental Example 1: Oligomerization Reaction According to Reaction Temperature Control The results of Examples 6 to 10 are shown in the following Table 3.

TABLE 3

|  | Reaction Temperature ° C. | Activity kg/molCr/hr | 1-C6 wt % | 1-C8 wt % | 1-C6 + 1-C8 wt % |
|---|---|---|---|---|---|
| Example 6 | 70 | 141,155 | 26 | 62 | 88 |
| Example 7 | 80 | 133,684 | 28 | 57 | 85 |
| Example 8 | 90 | 145,191 | 31 | 54 | 85 |
| Example 9 | 100 | 195,526 | 39 | 45 | 84 |
| Example 10 | 110 | 177,405 | 45 | 39 | 84 |

Referring to Table 3, in Example 6, the reaction was performed with the oligomerization reaction temperature of 70° C., and the ratio of 1-hexene and 1-octene was about 1:3. By performing the reaction while slowly increasing the reaction temperature from 70° C. to 110° C., the production ratio of 1-hexene and 1-octene was changed with tendency, and the weight ratio of 1-hexene and 1-octene was gradually changed from about 1:3 to about 1:0.9.

Conventionally, since the production ratio of 1 hexene and 1-octene was controlled via the mixing ratio of a catalyst for preparing 1-hexene and a catalyst for preparing 1-octene, the production ratio may not be easily changed during factory operation, by-products may be produced due to interaction between catalysts, or activation decrease or over-activation may be generated. However, according to the oligomerization method provided by the present disclosure, the production ratio of 1-hexene and 1-octene may be simply controlled by controlling only the reaction temperature of oligomerization. The temperature control may be performed during factory operation or at initial setting, and there are quite a lot of merits.

While this invention has been particularly shown and described with reference to preferred embodiments thereof and drawings, it will be understood by those skilled in the art that various changes in form and details may be made therein without departing from the spirit and scope of the invention as defined by the appended claims.

The invention claimed is:
1. A method for preparing an oligomerization catalyst system, the method comprising:
preparing a catalyst composition by mixing a ligand compound comprising a diphosphine moiety of the following Formula 3, and an organic chromium compound; and
activating by mixing a co-catalyst and the catalyst composition for two or more minutes and less than five minutes at a temperature from 20 to 80° C.:

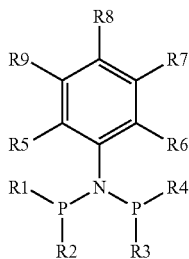

[Formula 3]

wherein in Formula 3:
R1 to R4 are each independently a C6 aryl or C7 alkylaryl group;
R5 is a methyl group;
R6 is a linear C2-C3 alkyl group or a linear C2-C3 alkenyl group; and
R7 to R9 are hydrogen.

2. The method for preparing an oligomerization catalyst system of claim 1, wherein an activating time of the co-catalyst and the catalyst composition is from two minutes or more to three minutes or less.

3. The method for preparing an oligomerization catalyst system of claim 1, wherein an activating temperature is from 20 to 80° C.

4. The method for preparing an oligomerization catalyst system of claim 1, wherein R7 to R9 of Formula 3 are hydrogen.

5. The method for preparing an oligomerization catalyst system of claim 1, wherein the transition metal compound comprises an organic chromium compound, and the organic chromium compound comprises at least one selected from the group consisting of chromium(III) acetyl acetonate, trichlorochromium tris tetrahydrofuran, chromium(III)-2-ethylhexanoate, chromium(III) tris (2,2,6,6-tetramethyl-3,5-heptanedionate), chromium(III) benzoyl acetonate, chromium(III) hexafluoro-2,4-pentanedionate and chromium (III) acetate hydroxide.

6. The method for preparing an oligomerization catalyst system of claim 1, wherein the co-catalyst is at least one selected from the compounds of the following Formulae 4 to 6:

$$-[Al(R_5)-O]_c-$$ [Formula 4]

wherein in the above Formula 4, $R_5$ is the same or different and is independently a halogen radical, a hydrocarbyl radical having 1 to 20 carbon atoms, or a halogen substituted hydrocarbyl radical having 1 to 20 carbon atoms, and c is an integer of at least 2;

$$D(R_6)_3$$ [Formula 5]

wherein in the above Formula 5, D is aluminum or boron, each $R_6$ is the same or different and is independently hydrogen, halogen, hydrocarbyl having 1 to 20 carbon atoms, or halogen substituted hydrocarbyl having 1 to 20 carbon atoms;

$$[L-H]^+[Q(E)_4]^-$$ [Formula 6]

wherein in the above Formula 6, L is a neutral Lewis base, $[L-H]^+$ is a brönsted acid, Q is boron or aluminum with an oxidation state of +3, and each E is independently aryl having 6 to 20 carbon atoms or alkyl having 1 to 20 carbon atoms, where at least one hydrogen atom is substituted with halogen, a hydrocarbyl having 1 to 20 carbon atoms, an alkoxy functional group or a phenoxy functional group or is unsubstituted.

7. A method for oligomerizing olefin, the method comprising:
performing a oligomerization reaction of olefin in a reaction temperature range of 30 to 150° C. in the presence of the oligomerization catalyst system prepared by the preparation method according to claim 1.

8. The method for oligomerizing olefin of claim 7, wherein the reaction temperature is in a range of 60 to 130° C.

9. The method for oligomerizing olefin of claim 7, wherein an activity of the catalyst system in a whole reaction temperature range is 100,000 kg/molCr/hr or more in a batch type process, and 100,000 kg/molCr or more in a continuous type process.

10. The method for oligomerizing olefin of claim 7, wherein an activity decreasing ratio of the catalyst system according to temperature increase is less than 6% in a whole reaction temperature range.

11. The method for oligomerizing olefin of claim 7, wherein selectivity of 1-hexene and 1-octene relative to a total amount of a product is 80 wt % or more in a whole reaction temperature range.

* * * * *